United States Patent
Siemering

(10) Patent No.: US 7,459,271 B2
(45) Date of Patent: Dec. 2, 2008

(54) METHOD FOR DETECTING WHETHER AN ORGANISM IS HOMOZYGOUS OR HETEROZYGOUS USING LABELLED PRIMERS AND RFLP

(75) Inventor: Kirby Siemering, Brunswick West (AU)

(73) Assignee: Murdoch Childrens Research Institute, Parkville (AU)

( * ) Notice: Subject to any disclaimer, the term of this patent is extended or adjusted under 35 U.S.C. 154(b) by 320 days.

(21) Appl. No.: 10/451,287

(22) PCT Filed: Dec. 20, 2001

(86) PCT No.: PCT/AU01/01643

§ 371 (c)(1), (2), (4) Date: Feb. 9, 2004

(87) PCT Pub. No.: WO02/50305

PCT Pub. Date: Jun. 27, 2002

(65) Prior Publication Data

US 2004/0132034 A1    Jul. 8, 2004

(30) Foreign Application Priority Data

Dec. 20, 2000  (AU) ................... PR2214

(51) Int. Cl.
  *C12Q 1/68*   (2006.01)
  *C12P 19/34*  (2006.01)
(52) U.S. Cl. .................. 435/6; 435/91.2
(58) Field of Classification Search .......... None
  See application file for complete search history.

(56) References Cited

U.S. PATENT DOCUMENTS 6,004,783 A    12/1999  Ausubel et al.
6,110,709 A *  8/2000   Ausubel et al. ............ 435/91.2
2003/0175729 A1* 9/2003  Van Eijk et al. ............. 435/6

FOREIGN PATENT DOCUMENTS

FR    2 718 461       10/1995
WO    9325563 A1      12/1993
WO    WO 98/12352     3/1998
WO    9853098 A1      11/1998
WO    9931272 A1      6/1999

OTHER PUBLICATIONS

Daly et al., Novel polymorphism in the FMR1 gene resulting in a "pseudodeletion" of FMR1 in a commonly used fragile X assay. J. Molec. Diag. (2000) 2:128-131.*
Bathum, L. et al., "A Dual Label Oligonucleotide Ligation Assay for Detection of the CYP2C19*1, CYP2C19*2, and CYP2C19*3 Alleles Involving Time-Resolved Fluorometry," *Therapeutic Drug Monitoring* 20(1):1-6, 1998.
Finch, J. et al., "PCR/RFLP Assay for Copy Number of Mutant and Wild-Type Alleles," *BioTechniques* 21(6):1055-1060, 1996.
Nikiforov, T. et al., "The Use of Phosphorothioate Primers and Exonuclease Hydrolysis for the Preparation of Single-stranded PCR Products and their Detection by Solid-phase Hybridization," *PCR Methods Appl.*, 3:285-291, 1994.
Shi, M. et al., "Technologies for Detecting Genetic Polymorphisms in Pharmacogenomics," *Molecular Diagnosis*, 4(4):343-351, 1999.
Shinder et al., A Sensitive Restriction Fragment Length Polymorphism Method to Detect CAA-AAA Mutations at Codon 61 of Ha-ras, Molecular Carcinogenesis, 1993, 263-267, vol. 7.

* cited by examiner

*Primary Examiner*—Kenneth R. Horlick
*Assistant Examiner*—David C Thomas
(74) *Attorney, Agent, or Firm*—Seed IP Law Group PLLC

(57) ABSTRACT

The invention is a method for detecting whether an organism is homozygous or heterozygous in a target nucleotide. The method combines hybridization of two differently labelled probes A and B on either side of a restriction site, restriction endonuclease digestion, and detection of the labels in the resulting digest. If an organism is: homozygous then the labels will be present in the ratio 1:1 or 1:0; or if heterozygous then the labels will be present in the ratio 1:2. Either immobilized array technology or electrophoretic separation may be used.

10 Claims, 4 Drawing Sheets

SEQUENCE LISTING

<160> NUMBER OF SEQ ID NOS: 49

<210> SEQ ID NO 1
<211> LENGTH: 21
<212> TYPE: DNA
<213> ORGANISM: Homo sapiens

<400> SEQUENCE: 1
cgcattatga tcctcgttgt g                                         21

<210> SEQ ID NO 2
<211> LENGTH: 29
<212> TYPE: DNA
<213> ORGANISM: Homo sapiens

<400> SEQUENCE: 2
aaagaaaata tcatctttgg tgtttccta                                 29

<210> SEQ ID NO 3
<211> LENGTH: 20
<212> TYPE: DNA
<213> ORGANISM: Artificial sequence
<220> FEATURE:
<223> OTHER INFORMATION: synthetic probe

<400> SEQUENCE: 3
gctgctcgtg gttaagctct                                           20

```
<210> SEQ ID NO 4
<211> LENGTH: 19
<212> TYPE: DNA
<213> ORGANISM: Artificial sequence
<220> FEATURE:
<223> OTHER INFORMATION: synthetic probe

<400> SEQUENCE: 4
cgtaccaatg gatgcggtc                                                   19

<210> SEQ ID NO 5
<211> LENGTH: 20
<212> TYPE: DNA
<213> ORGANISM: Artificial sequence
<220> FEATURE:
<223> OTHER INFORMATION: synthetic probe

<400> SEQUENCE: 5
gaggtcagtt cacgaagctc                                                  20

<210> SEQ ID NO 6
<211> LENGTH: 20
<212> TYPE: DNA
<213> ORGANISM: Artificial sequence
<220> FEATURE:
<223> OTHER INFORMATION: synthetic probe

<400> SEQUENCE: 6
gagttcccgt gcgttagatc                                                  20

<210> SEQ ID NO 7
<211> LENGTH: 20
<212> TYPE: DNA
<213> ORGANISM: Artificial sequence
<220> FEATURE:
<223> OTHER INFORMATION: synthetic probe

<400> SEQUENCE: 7
gcgactaggt ggctctaatc                                                  20

<210> SEQ ID NO 8
<211> LENGTH: 20
<212> TYPE: DNA
<213> ORGANISM: Artificial sequence
<220> FEATURE:
<223> OTHER INFORMATION: synthetic probe

<400> SEQUENCE: 8
agtcaagcta gatgccgatc                                                  20

<210> SEQ ID NO 9
<211> LENGTH: 20
<212> TYPE: DNA
<213> ORGANISM: Artificial sequence
<220> FEATURE:
<223> OTHER INFORMATION: synthetic probe

<400> SEQUENCE: 9
aaaccatcga ctcacgggat                                                  20

<210> SEQ ID NO 10
<211> LENGTH: 20
<212> TYPE: DNA
<213> ORGANISM: Artificial sequence
<220> FEATURE:
```

```
<223> OTHER INFORMATION: synthetic probe

<400> SEQUENCE: 10
atgcagcgta ggtatcgact                                                 20

<210> SEQ ID NO 11
<211> LENGTH: 20
<212> TYPE: DNA
<213> ORGANISM: Artificial sequence
<220> FEATURE:
<223> OTHER INFORMATION: synthetic probe

<400> SEQUENCE: 11
tacaacgatt gcctgcctgt                                                 20

<210> SEQ ID NO 12
<211> LENGTH: 20
<212> TYPE: DNA
<213> ORGANISM: Artificial sequence
<220> FEATURE:
<223> OTHER INFORMATION: synthetic probe

<400> SEQUENCE: 12
cacagagctg agtcggatat                                                 20

<210> SEQ ID NO 13
<211> LENGTH: 20
<212> TYPE: DNA
<213> ORGANISM: Artificial sequence
<220> FEATURE:
<223> OTHER INFORMATION: synthetic probe

<400> SEQUENCE: 13
tcagcgcgtg tcgttgcata                                                 20

<210> SEQ ID NO 14
<211> LENGTH: 20
<212> TYPE: DNA
<213> ORGANISM: Artificial sequence
<220> FEATURE:
<223> OTHER INFORMATION: synthetic probe

<400> SEQUENCE: 14
ttgaatcgtt tgaatcgcgg                                                 20

<210> SEQ ID NO 15
<211> LENGTH: 20
<212> TYPE: DNA
<213> ORGANISM: Artificial sequence
<220> FEATURE:
<223> OTHER INFORMATION: synthetic probe

<400> SEQUENCE: 15
catgcagctc gatctagcga                                                 20

<210> SEQ ID NO 16
<211> LENGTH: 20
<212> TYPE: DNA
<213> ORGANISM: Artificial sequence
<220> FEATURE:
<223> OTHER INFORMATION: synthetic probe

<400> SEQUENCE: 16
catgcagctc gatctagcga                                                 20
```

```
<210> SEQ ID NO 17
<211> LENGTH: 20
<212> TYPE: DNA
<213> ORGANISM: Artificial sequence
<220> FEATURE:
<223> OTHER INFORMATION: synthetic probe

<400> SEQUENCE: 17
cttgatacga ctgtcatggc                                               20

<210> SEQ ID NO 18
<211> LENGTH: 19
<212> TYPE: DNA
<213> ORGANISM: Artificial sequence
<220> FEATURE:
<223> OTHER INFORMATION: synthetic probe

<400> SEQUENCE: 18
cttgatacga ctgtcatgg                                                19

<210> SEQ ID NO 19
<211> LENGTH: 20
<212> TYPE: DNA
<213> ORGANISM: Artificial sequence
<220> FEATURE:
<223> OTHER INFORMATION: synthetic probe

<400> SEQUENCE: 19
agagcttaac cacgagcagc                                               20

<210> SEQ ID NO 20
<211> LENGTH: 20
<212> TYPE: DNA
<213> ORGANISM: Artificial sequence
<220> FEATURE:
<223> OTHER INFORMATION: synthetic probe

<400> SEQUENCE: 20
cgtaccaatg gatgcggtct                                               20

<210> SEQ ID NO 21
<211> LENGTH: 20
<212> TYPE: DNA
<213> ORGANISM: Artificial sequence
<220> FEATURE:
<223> OTHER INFORMATION: synthetic probe

<400> SEQUENCE: 21
agaccgcatc cattggtacg                                               20

<210> SEQ ID NO 22
<211> LENGTH: 20
<212> TYPE: DNA
<213> ORGANISM: Artificial sequence
<220> FEATURE:
<223> OTHER INFORMATION: synthetic probe

<400> SEQUENCE: 22
cgtaccaatg gatgcggtct                                               20

<210> SEQ ID NO 23
<211> LENGTH: 20
<212> TYPE: DNA
<213> ORGANISM: Artificial sequence
<220> FEATURE:
<223> OTHER INFORMATION: synthetic probe
```

```
<400> SEQUENCE: 23
gagcttcgtg aactgacctc                                               20

<210> SEQ ID NO 24
<211> LENGTH: 20
<212> TYPE: DNA
<213> ORGANISM: Artificial sequence
<220> FEATURE:
<223> OTHER INFORMATION: synthetic probe

<400> SEQUENCE: 24
gaggtcagtt cacgaagctc                                               20

<210> SEQ ID NO 25
<211> LENGTH: 20
<212> TYPE: DNA
<213> ORGANISM: Artificial sequence
<220> FEATURE:
<223> OTHER INFORMATION: synthetic probe

<400> SEQUENCE: 25
gatctaacgc acgggaactc                                               20

<210> SEQ ID NO 26
<211> LENGTH: 20
<212> TYPE: DNA
<213> ORGANISM: Artificial sequence
<220> FEATURE:
<223> OTHER INFORMATION: synthetic probe

<400> SEQUENCE: 26
gagttcccgt gcgttagatc                                               20

<210> SEQ ID NO 27
<211> LENGTH: 20
<212> TYPE: DNA
<213> ORGANISM: Artificial sequence
<220> FEATURE:
<223> OTHER INFORMATION: synthetic probe

<400> SEQUENCE: 27
gattagagcc acctagtcgc                                               20

<210> SEQ ID NO 28
<211> LENGTH: 20
<212> TYPE: DNA
<213> ORGANISM: Artificial sequence
<220> FEATURE:
<223> OTHER INFORMATION: synthetic probe

<400> SEQUENCE: 28
gcgactaggt ggctctaatc                                               20

<210> SEQ ID NO 29
<211> LENGTH: 20
<212> TYPE: DNA
<213> ORGANISM: Artificial sequence
<220> FEATURE:
<223> OTHER INFORMATION: synthetic probe

<400> SEQUENCE: 29
gatcggcatc tagcttgact                                               20

<210> SEQ ID NO 30
<211> LENGTH: 20
```

```
<212> TYPE: DNA
<213> ORGANISM: Artificial sequence
<220> FEATURE:
<223> OTHER INFORMATION: synthetic probe

<400> SEQUENCE: 30
agtcaagcta gatgccgatc                                                    20

<210> SEQ ID NO 31
<211> LENGTH: 20
<212> TYPE: DNA
<213> ORGANISM: Artificial sequence
<220> FEATURE:
<223> OTHER INFORMATION: synthetic probe

<400> SEQUENCE: 31
atcccgtgag tcgatggttt                                                    20

<210> SEQ ID NO 32
<211> LENGTH: 20
<212> TYPE: DNA
<213> ORGANISM: Artificial sequence
<220> FEATURE:
<223> OTHER INFORMATION: synthetic probe

<400> SEQUENCE: 32
aaaccatcga ctcacgggat                                                    20

<210> SEQ ID NO 33
<211> LENGTH: 20
<212> TYPE: DNA
<213> ORGANISM: Artificial sequence
<220> FEATURE:
<223> OTHER INFORMATION: synthetic probe

<400> SEQUENCE: 33
agtcgatacc tacgctgcat                                                    20

<210> SEQ ID NO 34
<211> LENGTH: 20
<212> TYPE: DNA
<213> ORGANISM: Artificial sequence
<220> FEATURE:
<223> OTHER INFORMATION: synthetic probe

<400> SEQUENCE: 34
atgcagcgta ggtatcgact                                                    20

<210> SEQ ID NO 35
<211> LENGTH: 20
<212> TYPE: DNA
<213> ORGANISM: Artificial sequence
<220> FEATURE:
<223> OTHER INFORMATION: synthetic probe

<400> SEQUENCE: 35
acaggcaggc aatcgttgta                                                    20

<210> SEQ ID NO 36
<211> LENGTH: 20
<212> TYPE: DNA
<213> ORGANISM: Artificial sequence
<220> FEATURE:
<223> OTHER INFORMATION: synthetic probe

<400> SEQUENCE: 36
```

-continued

```
tacaacgatt gcctgcctgt                                               20

<210> SEQ ID NO 37
<211> LENGTH: 20
<212> TYPE: DNA
<213> ORGANISM: Artificial sequence
<220> FEATURE:
<223> OTHER INFORMATION: synthetic probe

<400> SEQUENCE: 37
atatccgact cagctctgtg                                               20

<210> SEQ ID NO 38
<211> LENGTH: 20
<212> TYPE: DNA
<213> ORGANISM: Artificial sequence
<220> FEATURE:
<223> OTHER INFORMATION: synthetic probe

<400> SEQUENCE: 38
cacagagctg agtcggatat                                               20

<210> SEQ ID NO 39
<211> LENGTH: 20
<212> TYPE: DNA
<213> ORGANISM: Artificial sequence
<220> FEATURE:
<223> OTHER INFORMATION: synthetic probe

<400> SEQUENCE: 39
tatgcaacga cacgcgctga                                               20

<210> SEQ ID NO 40
<211> LENGTH: 20
<212> TYPE: DNA
<213> ORGANISM: Artificial sequence
<220> FEATURE:
<223> OTHER INFORMATION: synthetic probe

<400> SEQUENCE: 40
tcagcgcgtg tcgttgcata                                               20

<210> SEQ ID NO 41
<211> LENGTH: 20
<212> TYPE: DNA
<213> ORGANISM: Artificial sequence
<220> FEATURE:
<223> OTHER INFORMATION: synthetic probe

<400> SEQUENCE: 41
ccgcgattca aacgattcaa                                               20

<210> SEQ ID NO 42
<211> LENGTH: 20
<212> TYPE: DNA
<213> ORGANISM: Artificial sequence
<220> FEATURE:
<223> OTHER INFORMATION: synthetic probe

<400> SEQUENCE: 42
ttgaatcgtt tgaatcgcgg                                               20

<210> SEQ ID NO 43
<211> LENGTH: 20
<212> TYPE: DNA
<213> ORGANISM: Artificial sequence
```

```
<220> FEATURE:
<223> OTHER INFORMATION: synthetic probe

<400> SEQUENCE: 43
tcgctagatc gagctgcatg                                                 20

<210> SEQ ID NO 44
<211> LENGTH: 20
<212> TYPE: DNA
<213> ORGANISM: Artificial sequence
<220> FEATURE:
<223> OTHER INFORMATION: synthetic probe

<400> SEQUENCE: 44
catgcagctc gatctagcga                                                 20

<210> SEQ ID NO 45
<211> LENGTH: 20
<212> TYPE: DNA
<213> ORGANISM: Artificial sequence
<220> FEATURE:
<223> OTHER INFORMATION: synthetic probe

<400> SEQUENCE: 45
tgtgcgatcc tactgaccgt                                                 20

<210> SEQ ID NO 46
<211> LENGTH: 20
<212> TYPE: DNA
<213> ORGANISM: Artificial sequence
<220> FEATURE:
<223> OTHER INFORMATION: synthetic probe

<400> SEQUENCE: 46
acggtcagta ggatcgcaca                                                 20

<210> SEQ ID NO 47
<211> LENGTH: 20
<212> TYPE: DNA
<213> ORGANISM: Artificial sequence
<220> FEATURE:
<223> OTHER INFORMATION: synthetic probe

<400> SEQUENCE: 47
gccatgacag tcgtatcaag                                                 20

<210> SEQ ID NO 48
<211> LENGTH: 20
<212> TYPE: DNA
<213> ORGANISM: Artificial sequence
<220> FEATURE:
<223> OTHER INFORMATION: synthetic probe

<400> SEQUENCE: 48
cttgatacga ctgtcatggc                                                 20

<210> SEQ ID NO 49
<211> LENGTH: 20
<212> TYPE: DNA
<213> ORGANISM: Artificial sequence
<220> FEATURE:
<223> OTHER INFORMATION: synthetic probe

<400> SEQUENCE: 49
acgcagtgag tagcatcctg                                                 20
```

METHOD FOR DETECTING WHETHER AN ORGANISM IS HOMOZYGOUS OR HETEROZYGOUS USING LABELLED PRIMERS AND RFLP

FIELD OF THE INVENTION

The present invention relates generally to a method for detecting the presence or absence of one or more nuclcotides in a target nucleotide sequence. More particularly, the present invention contemplates a diagnostic assay,for the presence or absence of a particular mutation or polymorphism in a target nucleotide sequence. Even more particularly, the present invention combines differential hybridization or restriction endonuclease digestion with either immobilized array technology or electrophoretic separation to detect the presence or absence of a mutation or polymorphism in a target nucleotide sequence. The present invention further provides a kit to facilitate conducting the diagnostic assay as well as means, and more particularly data processing-assisted means, to automate or semi-automate the performance of the diagnostic assay.

BACKGROUND OF THE INVENTION

Reference to any prior art in this specification is not, and should not be taken as, an acknowledgment or any form of suggestion that this prior art forms part of the common general knowledge in Australia or any other country.

The increasing sophistication of recombinant DNA technology is greatly facilitating research and development in the medical, veterinary, agricultural and horticultural industries. This is particularly the case in the area of diagnostics for human disease conditions. As a greater understanding of genomics is achieved and with the completion or near completion of genome sequencing for a range of animals and mammals, including humans, and a range of microorganisms, there will be greater opportunities to develop diagnostic assays for a wide range of genetic based conditions.

Diagnostic techniques based on nucleic acid hybridization are unparalleled in their ability to identify and quantify genetic material of particular organisms or groups of genetically related organisms. The provision of DNA microfabricated array (micro-array) techniques now allows an "order of magnitude" increase in speed and specificity for this kind of gene-based analysis. For example, reference may be made to Southern (WO 89/10977; U.S. Pat. No. 6,045,270), Chee et al. (U.S. Pat. No. 5,837,832), Cantor et al. (U.S. Pat. No. 6,007,987) and Fodor et al. (U.S. Pat. No. 5,871,928).

Until recently, the nucleic acid probes used in nucleic acid hybridizations were mostly obtained empirically by isolating nucleic acid fragments from targeted organisms or genes. However, it is now possible to design and synthesize nucleic acid probes using data from the international sequence databases (e.g. the GenBank and EMBL databases). These databases of known gene sequences have been increasing tenfold in size every five years for many years and now contain a representative sample of most genes and most major groups of organisms.

Generally, DNA micro-arrays use spots of detector oligonucleotides or probes positioned in arrays on a solid support, typically a glass wafer. The probes are allowed to hybridize with sample nucleic acids, which contain the target nucleic acids and which have been fluorescently labelled. The probes and target nucleic acids of the sample are allowed to hybridize under conditions that only detect exact or almost exact complementarity between the probes and the target nucleic acids. If a target nucleic acid complements and hybridizes to a particular probe in the array, the spot will fluoresce. Recording the fluorescence of the spots enables one to assess which target sequences are present in the nucleic acids mixture.

Sequence information, obtained from native RNA or DNA molecules, is used to determine the sequence of the synthesized oligonucleotide probes and this information is usually stored in computer databases and manipulated using software. Each probe is synthesized so that it contains nucleotides in any order (sequence) that matches a part of a known native nucleotide sequence or the complement of a part of that sequence. Oligonucleotide probes used in conventional arrays are typically 10-25 nucleotides long.

Currently oligonucleotide probes are most commonly used in micro-arrays to identify and quantify the mRNA transcripts from genes. These micro-arrays usually contain probes representing several different target sequences from each gene sequence and these probes are usually chosen to be target specific (i.e. they hybridize with just one target polynucleotide). Thus, these micro-arrays contain many more probes than the number of target polynucleotides they are designed to detect.

Compared to conventional nucleic acid analysis techniques including restriction fragment length polymorphism (RFLP) analysis and the polymerase chain reaction (PCR), DNA micro-arrays provide a facile and rapid means of detecting and measuring the expression of different genes. They have also been used to detect variants of well characterized nucleic acid molecules (i.e. to detect genetic polymorphisms and genotypes). However, despite their promise as tools for diagnosing infectious diseases as well as genetic disorders, the development of micro-arrays for routine diagnosis appears to be slow. This is probably due to the relatively high cost of designing, developing and producing micro-arrays that could detect a larger number of target polynucleotides. New methods and reagents are, therefore, required to realize this promise and the present invention helps to meet that need.

In accordance with the present invention, the inventors have developed an improved assay system which can readily identify changes in nucleotides within a target nucleotide sequence and whether the mutation or polymorphism is present in homozygous or heterozygous form. The assay of the present invention has wide applicability for a range of genetic testing of humans, animals, microorganism and plants. The instant assay has particular utility in microarray-based assay procedures. Furthermore, many individual subjects can be analyzed on the same micro-array, which will allow large-scale genetic testing in a cost-effective manner.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

The present invention provides a means for detecting the presence or absence of a particular nucleotide or group of nucleotides in a target sequence. The assay comprises the selection or generation of forward and reverse amplification primers which, in one embodiment, are optionally both or singularly labelled with reporter molecules capable of providing separate identifiable signals, i.e. signals which can be distinguished with respect to each other. Alternatively, the amplification is conducted using unlabelled primers and detection is accomplished by hybridization of a probe differential labelled at its 5' and 3' termini. In one aspect, at least one of the pairs of primers further comprise tag sequences having sense and complementary sequences immobilized to a solid support. In addition, one or both primers may either introduce or remove a restriction endonuclease site within the target sequence depending on the presence or absence of a mutation sought to be detected. Alternatively, the primers may differentially hybridize to a target sequence. Following amplification to incorporate the tag sequence, if present, and reporter molecules and, in one embodiment, to add or remove a restriction endonuclease site, the amplified product is digested with the enzyme whose site has been introduced or removed and single-stranded forms subjected to immobilization conditions on the solid support. The presence or absence of the mutation or polymorphism determines whether the restriction endonuclease digests the target sequence and this in turn affects whether or not the reporter molecules on the respective primers are present on the captured amplified products. Due to the differential nature of the signals produced by the reporter molecules, a determination can be made as to the presence or absence of the mutation or polymorphism. One particular form of this embodiment is shown in FIG. 1. In another embodiment, differential restriction endonuclease digestion is assessed electrophoretically. In this embodiment, the tag sequence may still be present but is not required for electrophoretic separation. In one particular embodiment, amplification primers are employed without any reporter molecules being attached. In a further embodiment, one or both primers comprises chemically modified bases, nucleotides or phosphate linkages rendering the strand resistant to exonuclease digestion. This permits the generation of single-stranded DNA molecules. The presence or absence of a restriction endonuclease site is then determined by hybridizing a probe molecule comprising two different reporter molecules to a region encompassing the putative restriction site. This partial double-stranded DNA is then subjected to restriction endonuclease digestion and analyzed as above. One form of this particular embodiment is shown in FIG. 4.

Accordingly, one aspect of the present invention contemplates method for determining the presence or absence of a homozygous or heterozygous change in one or more nucleotides within a target nucleotide sequence, said method comprising:— amplifying said target nucleotide sequence using forward and reverse primers to produce an amplified product, wherein at least one of said primers is labelled with a reporter molecule capable of facilitating the provision of an identifiable signal which can be distinguished from another reporter molecule if both primers are labelled and wherein at least one primer and its complementary form comprises a complementary sequence to an oligonucleotide sequence anchored to a solid support and wherein one or more of said forward or reverse primers introduces, abolishes or hybridizes to a target site within the amplified product in the presence or absence of a change in one or more nucleotides, and subjecting said amplified product to detection means.

Another aspect of the present invention provides a method for determining the presence or absence of a homozygous or heterozygous change in one or more nucleotides within a target nucleotide sequence, said method comprising:

amplifying said target nucleotide sequence using forward and reverse primers to produce an amplified product wherein each of said primers is labelled with a reporter molecule capable of facilitating the provision of an identifiable signal which can be distinguished from each other and wherein at least one primer and its complementary form comprises a complementary sequence to an oligonucleotide sequence anchored to a solid support and wherein one or more said forward or reverse primers introduces or abolishes a restriction endonuclease site within the amplified product in the presence or absence of a change in one or more nucleotides;

digesting the amplified product with the restriction endonuclease whose site has been potentially introduced or abolished in said amplified product and subjecting single-stranded forms of the amplified product subjected to hybridization to conditions to permit annealing to a set of said immobilized oligonucleotides comprising oligonucleotides which are sense or complementary to a portion of the amplified sequence introduced by at least one primer; and detecting the relative proportion of signal by the reporter molecules wherein an equal proportion of different signals or the substantial presence of only one signal represents a bomozygous presence or absence of change in the target nucleotide sequence and wherein the presence of a differential signal represents a heterozygous presence or absence of said change in target nucleotide sequence.

In another embodiment, the present invention contemplates a method for determining the presence or absence of a homozygous or heterozygous change in one or more nucleotides within a target nucleotide sequence, said method comprising:— amplifying said target nucleotide sequence using forward and reverse primers to produce an amplified product wherein one primer comprises one or more chemically modified nucleotides, bases or phosphodiester bonds such that a nucleotide strand which extends from said primer is substantially resistant to exonuclease activity and wherein the other primer comprises a nucleotide sequences having sense and complementary sequences immobilized to a solid support and wherein one or more said forward or reverse primers introduces or abolishes a restriction endonuclease site within the amplified product in the presence or absence of a change in one or more nucleotides;

digesting the amplified product with an exonuclease to digest the strand not amplified by the primer comprising the exonuclease-resistant nucleotides, bases or phosphodiester linkages to generate a single-stranded nucleic acid molecule comprising the potential presence or absence of a restriction endonuclease site and a nucleotide sequence complementary to an oligonucleotide sequence immobilized to said solid support;

hybridizing to said single-stranded nucleic acid molecule a probe that contains complementarity to the restriction site that may have been introduced to generate a partial double-stranded molecule wherein the probe comprises two reporter molecules capable of facilitating the provision of identifiable signals which can be distinguished from each other;

digesting the partially double-stranded molecule with the restriction endonuclease whose site has been potentially introduced or abolished in said amplified product and subjecting the digested molecule to conditions to permit annealing to a set of said immobilized oligonucleotides comprising oligonucleotides which are sense or complementary to a portion of the amplified sequence introduced by at least one primer; and detecting the relative proportion of signal by the reporter molecules wherein an equal proportion of different signals or the substantial presence of only one signal represents a homozygous presence or absence of change in the target nucleotide sequence and wherein the presence of a differential signal represents a heterozygous presence or absence of said change in target nucleotide sequence.

Another aspect of the present invention contemplates a method for determining the presence or absence of a homozygous or heterozygous change in one or more nucleotides within a target nucleotide sequence, said method comprising:

amplifying said target nucleotide sequence using forward and reverse primers to produce an amplified product wherein each of said primers is labelled with a reporter molecule capable of facilitating the provision of an identifiable signal which can be distinguished from each other and wherein one or more of said forward or reverse primers introduces or abolishes a restriction endonuclease site within the amplified product in the presence or absence of a change in one or more nucleotides; and digesting the amplified product with the restriction endonuclease whose site has been potentially introduced or abolished in said amplified product and subjecting the amplified product subjected to digestion to conditions to permit electrophoretic separation of said digested products wherein the pattern of electrophoretic separation and/or the pattern of reporter molecule signaling is indicative of the homozygous presence or absence or the heterozygous presence or absence of said change in target sequence.

In a related embodiment, the present invention provides a method for determining the presence or absence of a homozygous or heterozygous change in one or more nucleotides within a target nucleotide sequence such as but not limited to, said method comprising:— amplifying said target nucleotide sequence using forward and reverse primers to produce an amplified product wherein one or more of said forward or reverse primers introduces or abolishes a restriction endonuclease site within the amplified product in the presence or absence of a change in one or more nucleotides; and digesting the amplified product with the restriction endonuclease whose site has been potentially introduced or abolished in said amplified product and subjecting the amplified product subject to digestion to conditions to permit electrophoretic separation of said digested products wherein the pattern of electrophoretic separation is indicative of the homozygous presence or absence or the heterozygous presence or absence of said change in target sequence.

A further aspect of the present invention provides a method for determining the presence or absence of a homozygous or heterozygous change in one or more nucleotides within a target nucleotide sequence, said method comprising:

amplifying said target nucleotide sequence using forward and reverse primers to produce an amplified product wherein each of said primers is labelled with a reporter molecule capable of facilitating the provision of an identifiable signal which can be distinguished from each other and wherein at least one primer and its complementary form comprises a complementary sequence to an oligonucleotide sequence anchored to a solid support and wherein one or more said forward or reverse primers introduces a restriction endonuclease site within the amplified product in the absence of a change in one or more nucleotides;

digesting the amplified product with the restriction endonuclease whose site has been potentially introduced in said amplified product and subjecting single-stranded forms of the amplified product subjected to hybridization to conditions to permit annealing to a set of said immobilized oligonucleotides comprising oligonucleotides which are complementary to a portion of at least one primer sequence or its complementary sequence; and detecting the relative proportion of signal by the reporter molecules wherein an equal proportion of different signals or the substantial presence of only one signal represents a homozygous presence or absence of change in the target nucleotide sequence and wherein the presence of a differential signal represents a heterozygous presence or absence of said change in target nucleotide sequence.

Yet another aspect of the present invention further provides an assay device for determining the presence or absence of a nucleotide or group of nucleotides in a nucleic acid molecule comprising an array of immobilized oligonucleotides each complementary to a nucleotide sequence within an amplified product digested by one or more restriction endonucleases and means to screen for the hybridization of a target sequence to the immobilized oligonucleotide array.

DETAILED DESCRIPTION OF THE PREFERRED EMBODIMENTS

Figure 1:
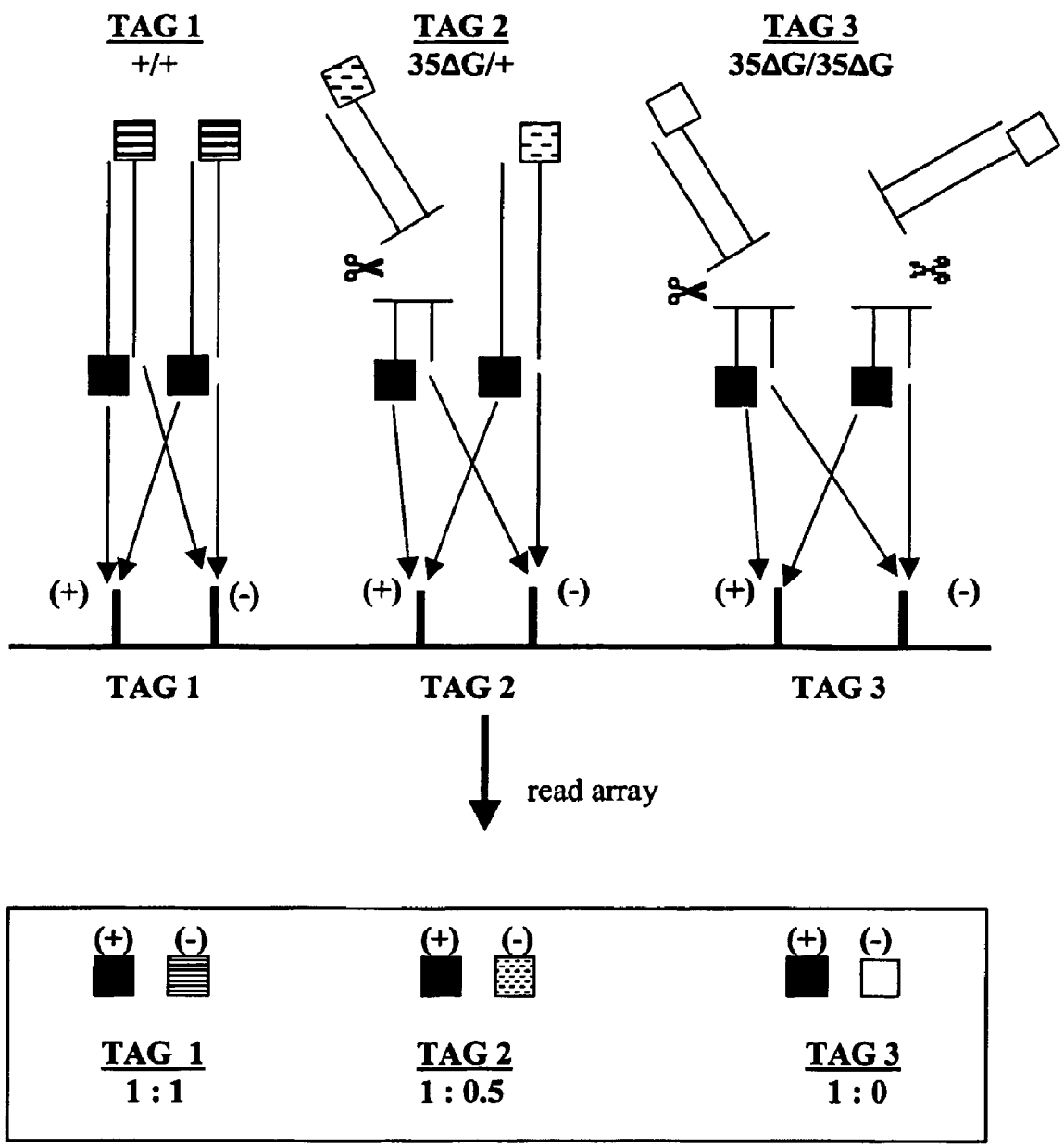
FIG. 1 is a diagrammatic representation of the genetic assay to determine the homozygous presence or absence or the presence in heterozygous form of the 35ΔG mutation in the connexin 26 gene.

The present invention provides inter alia a genetic assay to determine the homozygous presence or absence of a particular nucleotide or sequence of nucleotides and whether a particular nucleotide or nucleotide sequence is present in heterozygous form.

Accordingly, one aspect of the present invention contemplates a method for determining the presence or absence of a homozygous or heterozygous change in one or more nucleotides within a target nucleotide sequence, said method comprising:— amplifying said target nucleotide sequence using forward and reverse primers to produce an amplified product, wherein at least one of said primers is labelled with a reporter molecule capable of facilitating the provision of an identifiable signal which can be distinguished from another reporter molecule if both primers are labelled, and wherein at least one primer and its complementary form comprises a complementary sequence to an oligonucleotide sequence anchored to a solid support, and wherein one or more of said forward or reverse primers introduces, abolishes or hybridizes to a target site within the amplified product in the presence or absence of a change in one or more nucleotides, and subjecting said amplified product to detection means.

Preferably, the forward and reverse primers introduce or abolish a restriction endonuclease site.

Accordingly, this aspect of the present invention provides a method for determining the presence or absence of a homozygous or heterozygous change in one or more nucleotides within a target nucleotide sequence, said method comprising:

amplifying said target nucleotide sequence using forward and reverse primers to produce an amplified product wherein each of said primers is labelled with a reporter molecule capable of facilitating the provision of an identifiable signal which can be distinguished from each other and wherein at least one primer and its complementary form comprises a complementary sequence to an oligonucleotide sequence anchored to a solid support and wherein one or more said forward or reverse primers introduces or abolishes a restriction endonuclease site within the amplified product in the presence or absence of a change in one or more nucleotides;

digesting the amplified product with the restriction endonuclease whose site has been potentially introduced or abolished in said amplified product and subjecting single-stranded forms of the amplified product subjected to hybridization to conditions to permit annealing to a set of said immobilized oligonucleotides comprising oligonucleotides which are sense or complementary to a portion of the amplified sequence introduced by at least one primer; and detecting the relative proportion of signal by the reporter molecules wherein an equal proportion of different signals or the substantial presence of only one signal represents a homozygous presence or absence of change in the target nucleotide sequence and wherein the presence of a differential signal represents a heterozygous presence or absence of said change in target nucleotide sequence.

In a related embodiment, differential restriction endonuclease digestion may be determined electrophoretically.

Accordingly, another aspect of the present invention contemplates a method for determining the presence or absence of a homozygous or heterozygous change in one or more nucleotides within a target nucleotide sequence, said method comprising:

amplifying said target nucleotide sequence using forward and reverse primers to produce an amplified product wherein each of said primers are labelled with a reporter molecule capable of facilitating the provision of an identifiable signal which can be distinguished from each other and wherein one or more of said forward or reverse primers introduces or abolishes a restriction endonuclease site within the amplified product in the presence or absence of a change in one or more nucleotides; and digesting the amplified product with the restriction endonuclease whose site has been potentially introduced or abolished in said amplified product and subjecting the digested amplified product to conditions to permit electrophoretic separation of said digested products wherein the pattern of electrophoretic separation and/or the pattern of reporter molecule signaling is indicative of the homozygous presence or absence or the heterozygous presence or absence of said change in target sequence.

In a related embodiment, where electrophoretic separation is employed, the amplification primers are not labelled with a reporter molecule and/or tag sequence. According to this embodiment, the present invention contemplates a method for determining the presence or absence of a homozygous or heterozygous change in one or more nucleotides within a target nucleotide sequence such as but not limited to, said method comprising:— amplifying said target nucleotide sequence using forward and reverse primers to produce an amplified product wherein one or more of said forward or reverse primers introduces or abolishes a restriction endonuclease site within the amplified product in the presence or absence of a change in one or more nucleotides; and digesting the amplified product with the restriction endonuclease whose site has been potentially introduced or abolished in said amplified product and subjecting the amplified product subject to digestion to conditions to permit electrophoretic separation of said digested products wherein the pattern of electrophoretic separation is indicative of the homozygous presence or absence or the heterozygous presence or absence of said change in target sequence.

The present invention contemplates both the introduction of a restriction site or the abolition of a restriction site although the introduction of a restriction site in, for example, a wild-type or "non-mutation" sequence is preferred.

According to this preferred embodiment, the present invention provides a method for determining the presence or absence of a homozygous or heterozygous change in one or more nucleotides within a target nucleotide sequence, said method comprising:

amplifying said target nucleotide sequence using forward and reverse primers to produce an amplified product wherein each of said primers is labelled with a reporter molecule capable of facilitating the provision of an identifiable signal which can be distinguished from each other and wherein at least one primer and its complementary form comprises a complementary sequence to an oligonucleotide sequence anchored to a solid support and wherein one or more said forward or reverse primers introduces a restriction endonuclease site within the amplified product in the absence of a change in one or more nucleotides;

digesting the amplified product with the restriction endonuclease whose site has been potentially introduced in said amplified product and subjecting single-stranded forms of the amplified product subjected to hybridization to conditions to permit annealing to a set of said immobilized oligonucleotides comprising oligonucleotides which are complementary to a portion of each primer sequence or its complementary sequence; and detecting the relative proportion of signal by the reporter molecules wherein an equal proportion of different signals or the substantial presence of only one signal represents a homozygous presence or absence of change in the target nucleotide sequence and wherein the presence of a differential signal represents a heterozygous presence or absence of said change in target nucleotide sequence.

This aspect of the present invention further extends to electrophoretic separation to determine differential restriction endonuclease digestion.

The restriction site may be introduced or abolished by either the forward primer or the reverse primer. In one particularly useful embodiment, the forward primer is used to introduce a restriction site.

Accordingly, another aspect of the present invention is directed to a method for determining the presence or absence of a homozygous or heterozygous change in one or more nucleotides within a target nucleotide sequence, said method comprising:

amplifying said target nucleotide sequence using forward and reverse primers to produce an amplified product wherein said primers are labelled with a reporter molecule capable of facilitating the provision of an identifiable signal which can be distinguished from each other and wherein at least one primer and its complementary form comprises a complementary sequence to an oligonucleotide sequence anchored to a solid support and wherein said forward primer introduces a restriction endonuclease site within the amplified product in the absence of a change in one or more nucleotides; digesting the amplified product with the restriction endonuclease whose site has been potentially introduced in said amplified product and subjecting single-stranded forms of the amplified product subjected to hybridization to conditions to permit annealing to a set of said immobilized oligonucleotides comprising oligonucleotides which are complementary to a portion of the at least one primer sequence or its complementary sequence; and detecting the relative proportion of signal by the reporter molecules wherein an equal proportion of different signals or the substantial presence of only one signal represents a homozygous presence or absence of change in the target nucleotide sequence and wherein the presence of a differential signal represents a heterozygous presence or absence of said change in target nucleotide sequence.

In an alternative embodiment, the target sequence is amplified with an unlabelled set of primers. This is particularly useful for electrophoretic detection-based assays (e.g. for cystsic fibrosis). Alternatively, again unlabelled primers are used but one of the primers comprises one or more nucleotides which are chemically modified at the nucleotide or base level or wherein the phosphodiester linkage is modified so as to provide resistance to an exonuclease. A "chemically modified" base or nucleotide includes a nucleotide or base chemical analog. One example of a chemical modification is a phosphorothioate modification or a propyne modification. In essence, the chemical modification encompasses any modification which substantially inhibits the function of an exonuclease. In a particularly preferred embodiment, the chemical modification is a phosphorothioate modification.

The primers are also selected such that one or other of the primers introduce or abolish a restriction endonuclease site as described above. Furthermore, as above, at least one of the primers carries a sequence of nucleotides having a sense or complementary sequence in an oligonucleotide immobilized to a solid support.

After amplification, the resulting amplicon is subjected to exonuclease digestion. A DNA strand comprising the primer with one or more chemically modified nucleotide bases or phosphodiester linkages is generally immune from exonuclease cleavage. Accordingly, the exonuclease digests only the complementary strand leaving a single-stranded DNA comprising an introduced or abolished restriction site and a nucleotide sequence having a sense or complementary sequence in an oligonucleotide immobilized to a solid support. The single-stranded nucleotide sequence is then contacted by a nucleotide probe that contains complementarity to the restriction site that may have been introduced. The probe comprises two reporter molecules, preferably at its 5' and 3' ends and hybridizes to a region encompassing the introduced or abolished restriction endonuclease site. This hybridization results in a partial double-stranded molecule. This molecule is then subjected to digestion conditions. Depending on whether or not the restriction endonuclease site has been abolished will dictate whether or not the probe is cleaved. One aspect of this method is described in FIG. 4.

Accordingly, another aspect of the present invention contemplates a method for determining the presence or absence of a homozygous or heterozygous change in one or more nucleotides within a target nucleotide sequence, said method comprising:— amplifying said target nucleotide sequence using forward and reverse primers to produce an amplified product wherein one primer comprises one or more chemically modified nucleotides, bases or phosphodiester bonds such that a nucleotide strand which extends from said primer is substantially resistant to exonuclease activity and wherein the other primer comprises a nucleotide sequences having sense and complementary sequences immobilized to a solid support and wherein one or more said forward or reverse primers introduces or abolishes a restriction endonuclease site within the amplified product in the presence or absence of a change in one or more nucleotides;

digesting the amplified product with an exonuclease to digest the strand not amplified by the primer comprising the exonuclease-resistant nucleotides, bases or phosphodiester linkages to generate a single-stranded nucleic acid molecule comprising the potential presence or absence of a restriction endonuclease site and a nucleotide sequence complementary to an oligonucleotide sequence immobilized to said solid support;

hybridizing to said single-stranded nucleic acid molecule a probe that contains complementarity to the restriction site that may have been introduced to generate a partial double-stranded molecule wherein the probe comprises two reporter molecules capable of facilitating the provision of identifiable signals which can be distinguished from each other;

digesting the double-stranded molecule with the restriction endonuclease whose site has been potentially introduced or abolished in said amplified product and subjecting the digested molecule to conditions to permit annealing to a set of said immobilized oligonucleotides comprising oligonucleotides which are sense or complementary to a portion of the amplified sequence introduced by at least one primer; and detecting the relative proportion of signal by the reporter molecules wherein an equal proportion of different signals or the substantial presence of only one signal represents a homozygous presence or absence of change in the target nucleotide sequence and wherein the presence of a differential signal represents a heterozygous presence or absence of said change in target nucleotide sequence.

The target nucleotide sequence is generally in a eukaryotic cell such as a mammalian (including a human, primate, livestock animal, laboratory test animal or companion animal cell) or plant cell. In one particularly useful embodiment, the target nucleotide sequence is in a human cell. Furthermore, the target nucleotide sequence generally encompasses a nucleotide sequence of, for example, a structural gene or regulatory gene or 3' or 5' regulatory nucleotide sequences or promoter sequences which are associated with a particular disease condition. Disease conditions encompassed by this aspect of the present invention include but are not limited to disease conditions associated with one or more mutations in one gene or genetic sequence or in a number of known genes or genetic sequences. Examples of disease conditions contemplated herein for detection include metabolic disorders such as adreno-leukodystrophy, atherosclerosis, gaucher disease, gyrate atrophy, juvenile onset diabetes, obesity, paroxysmal nocturnal hemoglobinuria, phenylketonuria, refsum disease, tangler disease and haemochromatosis conditions involving transporters, channels and pumps such as cystic fibrosis, deafniess, diastrophic dysplasia, long-QT syndrome, Menkes syndrome, Pendred syndrome, polycystic kidney disease, sickle cell anemia, Wilson's disease and Zellweger syndrome, conditions involving signal transduction such as ataxia telangiectasia, baldness, Cockayne syndrome, glaucoma, tuberous sclerosis, Waardenburg syndrome and Werner syndrome; conditions involving the brain such as Alzheimer's disease, amyotrophic lateral sclerosis, Angleman syndrome, Charcot-Marie-Tooth disease, epilepsy, essential tremor, fragile X syndrome, Friedreich's ataxia, Huntington's disease, Niemann-Pick disease, Parkinson's disease, Prader-Willi syndrome, Rett syndrome, spinocerebella atrophy and William's syndrome; and conditions involving the skeleton such as Duchenne muscular dystrophy, Ellis-van Creveld syndrome, Marfan syndrome and myotonic dystrophy.

Some of the conditions contemplated herein are associated with aberrations in more than one gene or genetic sequence and, hence, an assay may require the interrogation of a number of genes for potential changes in nucleotide sequences associated with a disease condition.

Furthermore, the instant invention extends to detecting mutations and polymorphisms in a range of animal and plant cells. The present invention is particularly useful, for example, in screening for polymorphic variants in the genome of plants such as during the tissue culture stages of plant propagation. The ability to identify polymorphic variants in plants such as due to somaclonal variation will prevent unnecessary resources being wasted on plants with undesired properties.

A change in nucleotide sequence at the homozygous or heterozygous level is useful for determining the potential seriousness of the disease and in detecting potential carriers of the disease condition. Preferably, the change affects a single nucleotide such as a nucleotide substitution, addition or deletion.

The reporter molecule is any molecule capable of facilitating the provision of an identifiable signal. Suitable reporter molecules include but are not limited to chloramphenicol which can be acetylated with radioactive acetate groups, colourless galactosidases which may be hydrolyzed by galactosidases to yield coloured products, colourless glucuronides which may be hydrolyzed by glucuronides to yield coloured products and fluorescent products, luciferin which maybe oxidized by luciferase to release photons and green fluorescent protein which may be irradiated by U.V. light to emit photons and to fluoresce. A range of other enzyme-mediated, fluorescent, chemiluminescent and radioactive markers may also be employed. The reporter molecule may, therefore, directly or indirectly provide a signal.

Any restriction endonuclease site may be introduced. Suitable sites are recognized by the following restriction enzymes: AatI, AatII, AauI, Acc113I, Acc16I, Acc65I, AccB1I, AccB7I, AccBSI, AccI, AccII, AccIII, AceIII, AciI, AclI, AClNI, AcMWI, AcsI, AcyI, AdeI, AfaI, AfeI, AflII, AflIII, AgeI, AhaIII, AhdI, AluI, Alw21I, Alw26I, Alw44I, AlwI, AlwNI, Ama87I, AocI, AorflHI, ApaBI, ApaI, ApaLI, ApoI, AscI, AseI, AsiAI, AsnI, Asp700I, Asp718I, AspEI, AspHI, AspI, AspLEI, AspS9I, AsuC2I, AsuHPI, AsuI, AsuII, AsuNHI, AvaI, AvaII, AvaflI, AviII, AvrII, AxyI, BaeI, BalI, BamHI, BanI, BanII, Ban If, BbeI, BbiII, BbrPI, BbsI, BbuI, Bbv12I, BbvCI, BbvI, BbviI, BccI, Bce83I, BcefI, BcgI, BciVI, BclI, BcnI, BcoI, BcuI, BetI, BfaI, BfI, BfmI, BfrI, BglI, Bglu, BinI, BlnI, BipI, Bme18I, BmgI, BmrI, BmyI, BpiI, BpRI, BpmI, Bpu10I, Bpu1102I, Bpu14I, BpuAI, Bsa29I, BsaAI, BsaBI, BsaHI, BsaI, BsaJI, BsaMI, BsaOI, BsaWI, BsaXI, BsbI, Bsc4I, BscBI, BscCI, BscFI, BscGI, BscI, Bse118I, BseII, Bse21I, Bse3DI, Bse8I, BseAI, BseCI, BseDI, BseGI, BseLI, BseMI, BseNI, BsePI, BseRI, BseX3I, BsgI, Bsh1236I, Bsh1285I, Bsh1365I, BshI, BshNI, BsiBI, BsiCI, BsiEI, BsiHKAI, BsiI, BsiLI, BsiMI, BsiQI, BsiSI, BsiWI, BsiXI, BsiYI, BsiZI, BslI, BsmAI, BsmBI, BsmFI, BsmI, BsoBI, Bsp106I, Bsp119I, Bsp120I, Bsp1286I, Bsp13I, Bsp1407I, Bsp143I, Bsp1431I, Bsp1720I, Bsp19I, Bsp24I, Bsp68I, BspA2I, BspCI, BspDI, BspEI, BspGI, BspHI, BspLI, BspLU11I, BspMI, BspMfI, BspTI, BspXI, BsrBI, BsrBR1, BsrDI, BsrFI, BsrGI, BsrI, BsrSI, BssAI, BssHII, BssKI, BssNAI, BssSI, BssT1I, Bst1107I, Bst2BI, Bst2UI, Bst4CI, Bst71I, Bst98I, BstACI, BstAPI, BstBAI, BstBI, BstDEI, BstDSI, BstEII, BstF5I, BstH2I, BstHPI, BstMCI, BstNI, BstNSI, BstOI, BstPI, BstSFI, BstSNI, BstUI, BstX2I, BstXI, BstYI, BstZ17I, BstZI, Bsu15I, Bsu36I, Bsu6I, BsuRI, BtgI, BtsI, Cac8I, CauII, CbiI, CciNI, Cem, CfoI, Cfr10I, Cfr13I, Cfr42I, Cfr9I, CfrI, CjeI, CjePI, ClaI, CpoI, Csp45I, Csp6I, CspI, CviJI, CviRI, CvnI, DdeI, DpnI, DpnII, DraI, DraII, DraIII, DrdI, DrdII, DsaI, DseDI, EaeI, EagI, Eaml 1041, Eam1105I, EarI, EciI, Ecl136JI, EclHKI, EciXI, Eco10SI, Eco130I, Eco147I, Eco24I, Eco255I, Eco31I, Eco32I, Eco47I, Eco47HI, Eco52I, Eco57I, Eco64I, Eco72I, Eco81I, Eco88I, Eco91I, EcoICR1, EcoNI, EcoO109I, EcoO65I, EcoRI, EcoRII, EcoRV, EcoTl4I, EcoT22I, EcoT38I, EgeI, EheI, ErhI, Esp1396I, Esp3I, EspI, FauI, FauNDI, FbaI, FinI, Fnu4HI, FnuDII, FokI, FriOI, FseI, Fsp4HI, FspI, GdiII, GsuI, HaeI, HaeII, HaeIII, HaeIV, HapH, HgaI, HgiAI, HgiCI, HgiEI, HgiEII, HgiJII, HhaI, HinlI, Hin2I, Hin4I, Hin6I, HincII, HindIII, HindIII, HinfI, HinP1I, HpaI, HpaiI, HphI, Hsp92I, Hsp921I, HspAI, ItaI, KasI, Kpn2I, KpnI, Ksp22I, Ksp632I, KspAI, KspI, Kzo9I, LspI, MaeI, MaeII, MaeIII, MamI, MbiI, MboI, MboiI, McrI, MfeI, MflL, MlsI, MluL, MluNI, Mly113I, MmeI, MnlI, Mph1103I, MroI, MroNI, MroXI, MscI, MseI, MsiI, Msp17I, MspA1I, MspCI, MspI, MspR9I, MstI, MunI, Mva1269I, MvaI, MvnI, MwoI, NaeI, NarI, NciI, NcoI, NdeI, NdeII, NgoAIV, NgoMIV (previously known as NgoMI), NheI, NlaIII, NlaV, NotI, NruGI, NruI, NsbI, NsiI, NspBH, NspI, NspV, PacI, PaeI, PaeR7I, PagI, PalI, PauI, Pfl108I, Pfl1231I, PflFI, PflMI, PinAI, Ple19I, PleI, PmaCI, Pme55I, PmeI, PmlI, Ppu10I, PpuMI, PshAI, PshBI, Psp124BI, Psp1406I, Psp5U, PspAI, PspEI, PspLI, PspN4I, PspOMI, PspPPI, PstI, PvuI, PvuII, RcaI, RleAI, RsaI, RsrII, SacI, SacfI, SalI, SanDI, SapI, Sau3AI, Sau96I, SauI, SbfI, ScaI, SchI, ScrFI, SdaI, SduI, SecI, SexAI, SfaNI, SfcI, SfeI, SfiI, SfoI, Sfr274I, Sft303I, SfuI, SgtI, SgrAI, SimI, SinI, SmaI, SmiI, SmlI, SnaBI, SnaI, SpeI, SphI, SplI, SrfI, Sse8387I, Sse8647I, Sse9I, SseBI, SspBI, SspI, SstI, SstHI, StuI, StyI, SunI, SwaI, TaiI, TaqI, TaqiI, TatI, TauI, TfiI, ThaI, Tru1I, Tru9I, TscI, TseI, Tsp45I, Tsp4CI, Tsp509I, TspEI, TspRI, Tth111I, Tth111II, TthHB8I, UbaDI, UbaEI, UbaLI, UbaOI, Van91I, Yha464I, VneI, VspI, XagI, XbaI, XcmI, XhoI, XhoII, XmaCI, XmaI, XmaIII and XmnI, Zsp2I.

The solid support is typically glass or a polymer, such as but not limited to, cellulose, ceramic material, nitrocellulose, polyacrylamide, nylon, polystyrene and its derivatives, polyvinylidene difluoride (PVDF), methacrylate and its derivatives, polyvinyl chloride or polypropylene. Nitrocellulose may also be used. Glass is particularly preferred. A solid support may also be a hybrid such as a nitrocellulose film supported on a glass or polymer matrix. Reference to a "hybrid" includes reference to a layered arrangement of two or more glass or polymer surfaces listed above. The solid support may be in the form of a membrane or tubes, beads, discs or microplates, or any other surface suitable for conducting an assay. Binding processes to immobilize the molecules are well-known in the art and generally consist of covalently binding (e.g. cross linking) or physically adsorbing the molecules to the solid substrate.

The term "complementary" refers to the topological capability or matching together of interacting surfaces of an oligonucleotide probe and its target oligonucleotide, which may be part of a larger polynucleotide. Thus, the target and its probe can be described as complementary, and furthermore, the contact surface characteristics are complementary to each other. Complementary includes base complementarity such as A is complementary to T or U, and C is complementary to G in the genetic code. However, this invention also encompasses situations in which there is non-traditional base-pairing such as Hoogsteen base pairing which has been identified in certain transfer RNA molecules and postulated to exist in a triple helix. In the context of the definition of the term "complementary", the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that hybridize less efficiently.

The term "oligonucleotide" as used herein refers to a polymer composed of a multiplicity of nucleotide residues (deoxyribonucleotides or ribonucleotides, or related structural variants or synthetic analogs thereof) linked via phosphodiester bonds (or related structural variants or synthetic analogs thereof). Thus, while the term "oligonucleotide" typically refers to a nucleotide polymer in which the nucleotide residues and linkages between them are naturally occurring, it will be understood that the term also includes within its scope various analogs including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 8 to 50 nucleotides, preferably 8 to 30 nucleotides, more preferably from about 10 to 20 nucleotides and still more preferably from about 11 to 17 nucleotides, but the term can refer to molecules of any length, although the term "polynucleotide" or "nucleic acid" is typically used for large oligonucleotides. Oligonucleotides may be prepared using any suitable method, such as, for example, the phosphotriester method as described in an article by Narang et al. (*Methods Enzymol.* 68: 90, 1979) and U.S. Pat. No. 4,356,270. Alternatively, the phosphodiester method as described in Brown et al. (*Methods Enzymol.* 68: 109, 1979) may be used for such preparation. Automated embodiments of the above methods may also be used. For example, in one such automated embodiment, diethylphosphoramnidites are used as starting materials and may be synthesized as described by Beaucage et al. (*Tetrahedron Letters* 22: 1859-1862, 1981). Reference also may be made to U.S. Pat. Nos. 4,458,066 and 4,500,707, which refer to methods for synthesizing oligonucleotides on a modified solid support. It is also possible to use a primer, which has been isolated from a biological source (such as a denatured strand of a restriction endonuclease digest of plasmid or phage DNA). In a preferred embodiment, the oligonucleotide is synthesized according to the method disclosed in U.S. Pat. No. 5,424,186 (Fodor et al.). This method uses lithographic techniques to synthesize a plurality of different oligonucleotides at precisely known locations on a substrate surface.

The terms "array" and in particular "DNA array" or "oligonucleotide array" refer to a substrate having oligonucleotide probes with different known sequences deposited at discrete known locations associated with its surface. For example, the substrate can be in the form of a two-dimensional substrate as described in U.S. Pat. No. 5,424,186. Such substrate may be used to synthesize two-dimensional spatially addressed oligonucleotide (matrix) arrays. Alternatively, the substrate may be characterized in that it forms a tubular array in which a two-dimensional planar sheet is rolled into a three-dimensional tubular configuration. The substrate may also be in the form of a microsphere or bead connected to the surface of an optic fibre as, for example, disclosed by Chee et al. in WO 00/39587. Oligonucleotide arrays have at least two different features and a density of at least 400 features per $cm^2$. In certain embodiments, the arrays can have a density of about 500, at least one thousand, at least 10 thousand, at least 100 thousand, at least one million or at least 10 million features per $cm^2$. For example, as stated above, the substrate may be silicon or glass and can have the thickness of a glass microscope slide or a glass cover slip, or may be composed of other synthetic polymers. Substrates that are transparent to light are useful when the method of performing an assay on the substrate involves optical detection. The term also refers to a probe array and the substrate to which it is attached that form part of a wafer.

The term "probe" refers to an oligonucleotide molecule that binds to a specific target sequence or other moiety of another nucleic acid molecule. Unless otherwise indicated, the term "probe" in the context of the present invention typically refers to an oligonucleotide probe that binds to another oligonucleotide or polynucleotide, often called the "target polynucleotide", through complementary base pairing. Probes can bind target polynucleotides lacking complete sequence complementarity with the probe, depending on the stringency of the hybridization conditions.

Oligonucleotide probes may be selected to be "substantially complementary" to a target sequence as defined herein. The exact length of the oligonucleotide probe will depend on many factors including temperature and source of probe and use of the method. For example, depending upon the complexity of the target sequence, the oligonucleotide probe may typically contain 8 to 50 nucleotides, preferably 8 to 30 nucleotides, more preferably from about 10 to 20 nucleotides and still more preferably from about 11 to 17 nucleotides capable of hybridization to a target sequence although it may contain more or fewer such nucleotides.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al. (Nucl. Acids Res. 25: 3389. 1997). A detailed discussion of sequence analysis can be found in Unit 19.3 of Ausubel et al. ("Current Protocols in Molecular Biology" John Wiley & Sons Inc, 1994-1998, Chapter 15.).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C)% (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The terms "target polynucleotide" or "target sequence" refer to a polynucleotide of interest (e.g. a single gene or polynucleotide) or a group of polynucleotides (e.g. a family of polynucleotides). The target polynucleotide can designate mRNA, RNA, eRNA, cDNA or DNA. The probe is used to obtain information about the target polynucleotide: whether the target polynucleotide has affinity for a given probe. Target polynucleotides may be naturally occurring or man-made nucleic acid molecules. Also, they can be employed in their unaltered state or as aggregates with other species. Target polynucleotides may be associated covalently or non-covalently, to a binding member, either directly or via a specific binding substance. A target polynucleotide can hybridize to a probe whose sequence is at least partially complementary to a sub-sequence of the target polynucleotide.

These terms are also used herein to refer to a chosen nucleotide sequence of at most 300, 250, 200, 150, 100, 75, 50, 30, 25 or at most 15 nucleotides in length. Target sequences include sequences of at least 8, 10, 15, 25, 30, 35, 45, 50, 60, 70, 80, 90, 100, 120, 135, 150, 175, 200, 250 and 300 nucleotides in length. Non-limiting examples of target sequences include, but are not restricted to, repeat sequences such as Alu repeat sequences, conserved or non-conserved regions of gene families, introns, promoter sequences including the Hogness Box and the TATA box, signal sequences, enhancers, protein-binding domains such as a homeobox, tymobox, polymorphisms and conserved protein domains or portions thereof.

Hybridization and/or reporter signal data are processed to determine the presence or absence of a restriction endonuclease site. In a preferred embodiment, a digital computer is employed to correlate specific positional labelling on the array with the presence of any of the target sequences for which the probes have specificity of interaction. The positional information is directly converted to a database indicating what sequence interactions have occurred. Data generated in hybridization assays are most easily analyzed with the use of a programmable digital computer. The computer program product generally contains a readable medium that stores the codes. Certain files are devoted to memory that includes the location of each feature and all the target sequences known to contain the sequence of the oligonucleotide probe at that feature. Computer methods for analyzing hybridization data from nucleic acid arrays is taught in International Patent Publication No WO 97/29212 and EP Publication 95307476.2. In a preferred embodiment, the prograrrmable computer would contain specialist software code and register data derived from the entire sequence database, or containing that part of the entire sub-sequence database that is relevant to the particular probe array, and from the pattern of hybridization will assess the probability that particular target sequences were present in the tested DNA sample.

The computer program product can also contain code that receives as input hybridization data from a hybridization reaction between a target sequence and an oligonucleotide probe. The computer program product can also include code that processes the hybridization data.

Data analysis can include the steps of determining, for example, the fluorescence intensity as a function of substrate position from the data collected, removing "outliers" (data deviating from a predetermined statistical distribution) and calculating the relative binding affinity of the target sequences from the remaining data. The resulting data can be displayed as an image with colour in each region varying according to the light emission or binding affinity between target sequences and probes therein.

In one embodiment, the amount of binding at each address is determined by examining the on-off rates of the hybridization. For example, the amount of binding at each address is determined at several time points after the nucleic acid sample is contacted with the array. The amount of total hybridization can be determined as a function of the kinetics of binding based on the amount of binding at each time point.

Persons of skill in the art can easily determine the dependence of the hybridization rate on temperature, sample agitation, washing conditions (e.g. pH, solvent characteristics, temperature) in order to maximise conditions for hybridisztion rate and signal to noise.

The computer program product also can include code that receives instructions from a programmer as input. The computer program product may also transform the data into a format for presentation.

In one embodiment, the computer program product for processing hybridization data comprises code that identifies for each target polynucleotide a combination of features in an oligonucleotide array whose probes facilitate specific detection of that polynucleotide; code that receives as input hybridization data from hybridization reactions between sample polynucleotides and the oligonucleotide probes in the array; code that processes the hybridisation data to determine whether the sample polynucleotides comprises any of the target polynucleotides by searching for hybridization patterns that match any of the predefined combinations of target sequences; codes that identify the presence of a reporter molecule-mediated signal; and a computer readable medium that stores the codes. It is not necessary to identify the sequence of respective oligonucleotide probes in each feature of the array. In this respect, the hybridization analysis software only requires as input which combination of features in the array corresponds to a particular target polynucleotide. However, in a preferred embodiment, the computer program product comprises code that receives as input the sequence of an oligonucleotide probe in each feature of an oligonucleotide array and code that receives as input a database that contains information on the presence or absence of target sequences in target polynucleotides.

Preferably the computer program product further comprises code that deduces the probability that the detected pattern of hybridization indicates the presence of a target polynucleotide.

The database of target sequences would be regularly updated and the part of it relevant to each particular set of probes forming each micro-array would also be updated for those using particular commercial applications of the invention.

The method of the present invention may also be modified to introduce one particular restriction endonuclease site but to abolish another site. This provides even more accuracy and a reduced likelihood of a false negative or false positive. In addition, it is not necessary that a primer has to introduce a restriction endonuclease site. A particular site may be naturally present in a target sequence.

The present invention further provides an assay device for determining the presence or absence of a nucleotide or group of nucleotides in a nucleic acid molecule comprising an array of immobilized oligonucleotides each complementary to a nucleotide sequence within an amplified product digested by one or more restriction endonucleases and means to screen for the hybridization of a target sequence to the immobilized oligonucleotide array. The assay device may also be packaged for sale and contain instructions for use.

The present invention is further described by the following non-limiting Examples.

EXAMPLE 1

Development of Genetic Deafness Assay: EcoRII Assay

In this assay, a mutation at nucleotide 35 in the connexin 26 gene is identified either in the homozygous or heterozygous state. The mutation is a deletion of a guanine at position 35. This mutation is referred to as "35 ΔG".

Two primers are developed, each labelled with a different reporter molecule and at least one comprising a nucleotide sequence matching and complementary to oligonucleotide sequences immobilized to a solid support. This sequence on the primer is referred to as a "tag" sequence. Conveniently, in one example, the GeneChip (registered trademark) is used incorporating GenFlex (trademark) Tag array. The primers comprise, therefore, a reporter molecule alone or linked to a tag sequence (having matching and complementary sequences immobilized to a solid support). In this example, one primer comprises a tag sequence linked to a nucleotide sequence complementary to a region flanking the 35ΔG region for the forward primer and a region downstream of this location for the reverse primer. In one example, the reverse primer introduces a base change in the wild-type sequence thus creating a EcoRII site. If the target sequence comprises a 35ΔG mutation then the EcoRII site is lost. This is because EcoRII recognizes the nucleotide sequence 5'CCWGG3' where W is A or T. In the connexin 26 gene, the nucleotide sequence recognized by EcoRII is 5'CCTGG3'. However, a 35ΔG mutation removes the G at the 3' position and, hence, amplification product from a 35ΔG sample will not digest but a wild-type sequence will digest. After amplification and digestion with EcoRII, single-stranded forms of the amplified product are exposed to the immobilized oligonucleotides on the solid support. This assay is shown in FIG. 1.

As can be observed, when the target sequence is homozygous wild-type, all the amplification product will be digested thus removing the reporter molecule associated with the reverse primer. The complementary (antisense) immobilized oligonucleotide (+) permits capture of the tag associated with the forward primer. The matching (sense) immobilized oligonucleotide (−) permits capture of the sequence complementary to the tag generated by extension of the reverse primer during PCR (ie the complementary strand to the strand generated by extension of the forward primer). Regardless of restriction enzyme digestion, the reporter molecule associated with the forward primer will always be detected at the (+) feature of the immobilized oligonucleotide pair specific for the tag associated with that forward primer. As the reporter molecule associated with the reverse primer has been cleaved away by EcoRII digestion, no reporter molecule will be detected at the (−) feature of the immobilized oligonucleotide pair, i.e. the ratio of signal from forward to reverse primer would be in the order of 1:0.

If the 35ΔG mutation is present in a homozygous state, there will be no digestion of any amplification product and both reporter molecules on both primers will be equally represented, i.e. in a ratio of about 1:1.

If the 35ΔG mutation is in the heterozygous state, then the amplification product from the nucleotide sequence carrying the mutation will not cleave but cleavage will occur in the amplification product from the nicleotide sequence not carrying the mutation. Therefore, about half of the molecules in the total amplification will be cleaved. Accordingly, the ratio of signal from forward to reverse primer will be approximately 1:0.5.

EXAMPLE 2

Development of Genetic Deafness Assay: DdeI Assay

In this assay, the same approach as adopted in Example 1 but a mutation is introduced to create a DdeI site in the 35ΔG sequence. A target variant would, therefore, be cleaved by DdeI, whereas the wild-type sequence would not.

EXAMPLE 3

Development of Genetic Deafness Assay: BclI Assay

The aim of this assay is to use a primer to change a cytosine to an adenine thus creating a BclI site in the Cx26 gene. The target nucleotide sequence is as follows:—
CGC ATT ATG ATC CTC GTT GTG (SEQ ID NO:1).

A reverse primer creates a mismatch such that the TGATCC sequence becomes TGATCA which is the recognition sequence for BclI. Wild-type amplification product based on this modified sequence is digestible by Bcli. A mutation in the ATG codon leading to genetic deafness results in the codon changing to ACG (i.e. a T→C substitution). This corresponds to an M34T substitution. The BclI site, i.e. TGATCA, becomes CGATCA and, hence, amplification product carrying this mutation is no longer digestible by BclI.

EXAMPLE 4

Development of Assay for Cystic Fibrosis

This assay is predicated on enzyme recognition sequences for XcmI and BstX1. The cystic fibrosis gene comprises the following target sequence:—
5'AAA GAA AAT ATC ATC TTT GGT GTT TCC TA (SEQ ID NO:2).

Mutations giving rise to a potential development of cystic fibrosis include a deletion of a phenylalanine residue at position 508, i.e. ΔF508. This results from a deletion of a CTT codon.

The first step is to use a reverse primer to introduce two A→C substitutions to create the XcmI site: CCA(N)$^9$TGG.

As a result, wild-type amplification product is digested by XcmI. If the CTT codon is deleted (see FIG. 2), then XcmI does not digest the amplified DNA.

Figure 2:
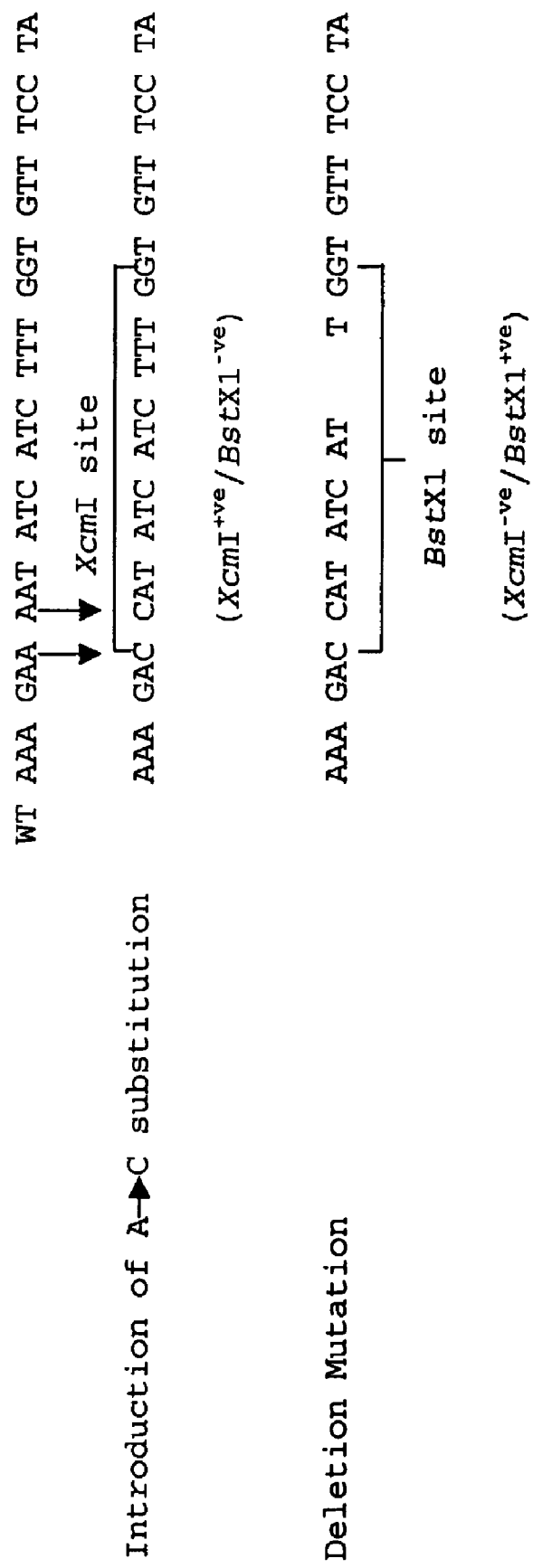
FIG. 2 is a diagrammatic representation showing (A) wild-type (WT) target sequence for genetic testing for cystic fibrosis; (B) the WT sequence carrying two A→C substitutions creating an XcmI site; (C) a CTT deletion destroys the XcmI site but creates a BstAI site.

BstX1 has the recognition sequence CCA(N)$^6$TGG. BstX1 does not digest the wild-type sequence (FIG. 2). A CTT deletion and the A→C substitutions creates a Bstm site. Accordingly, where the CTT deletion has occurred, the amplification product is XcmI$^{-ve}$/BstX1$^{+ve}$ whereas the wild-type is XcmI$^{+ve}$/BstX1$^{-ve}$.

Figure 3:
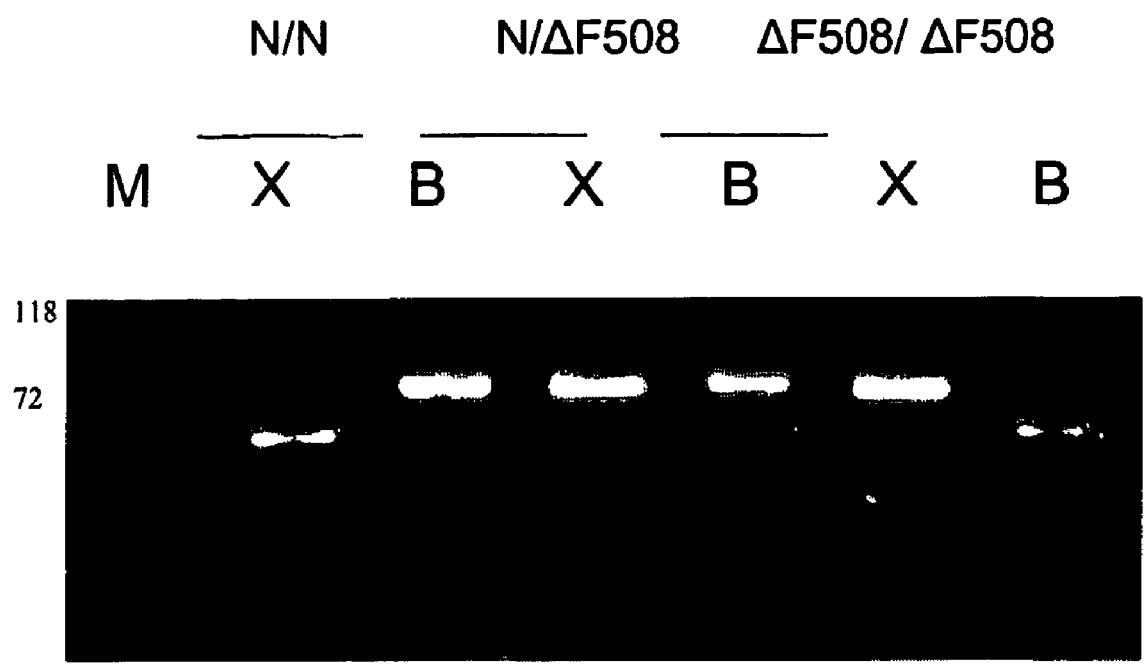
FIG. 3 is a photographic representation showing electrophoretic separation of amplified products following amplification of DNA putatively encoding a ΔF508 mutation. The target sequence is set forth in <400>2 (Example 4). X, XcmI; B, BstXI; m, marker; N/N, homozygous normal; ΔF508/ΔF508, homozygous mutation; N/ΔF508, heterozygous mutation.

This assay may be conducted using the solid array technology as in Examples 1-3 or may be used in conjunction with electrophoretic separation. The amplification primer sequences need not be labelled with a reporter molecule and/or a tag sequence. An example of electrophoretic separation is shown in FIG. 3. The differential restriction pattern can be seen between homozygous normal (N/N), homozygous abnormal (ΔF508/ΔF508) and heterozygous normal (N/ΔF508).

EXAMPLE 5

Combination Assay for Cystic Fibrosis

A combination assay is conducted using biochemical and genetic testing.

In the combination assay, all babies are subjected to a biochemical test for cystic fibrosis. Where there is no biochemical indication of a mutation, the baby is placed in a non-risk category. If the biochemical test suggests the presence of a mutation, then a genetic test is conducted such as outlined in Example 4. Gel electrophoresis (such as polyacrylamide or agarose gel electrophoresis) is carried out using one or both XcmI and/or BstXI or an array technology may be employed.

EXAMPLE 6

Development of Chip Technology

Table 1 provides a list of 15 tags which are used in conjunction with PCR oligos. Table 2 is a list of chip probes. These are sense and antisense capture probes which are immobilized to the array.

TABLE 1

| | Chip TAG list | | |
|---|---|---|---|
| 1 | ProbeSet01548 | GCTGCTCGTGGTTAAGCTCT [SEQ ID NO: 3] | High |
| 2 | ProbeSet00138 | CGTACCAATGGATGCGGTCT [SEQ ID NO: 4] | High |
| 3 | ProbeSet00357 | GAGGTCAGTTCACGAAGCTC [SEQ ID NO: 5] | High |
| 4 | ProbeSet00468 | GAGTTCCCGTGCGTTAGATC [SEQ ID NO: 6] | High |
| 5 | ProbeSet00512 | GCGACTAGGTGGCTCTAATC [SEQ ID NO: 7] | High |
| 6 | ProbeSet01873 | AGTCAAGCTAGATGCCGATC [SEQ ID NO: 8] | High |
| 7 | ProbeSet00007 | AAACCATCGACTCACGGGAT [SEQ ID NO: 9] | High |
| 8 | ProbeSet00156 | ATGCAGCGTAGGTATCGACT [SEQ ID NO: 10] | High |
| 9 | ProbeSet01052 | TACAACGATTGCCTGCCTGT [SEQ ID NO: 11] | High |
| 10 | ProbeSet01113 | CACAGAGCTGAGTCGGATAT [SEQ ID NO: 12] | High |

TABLE 1-continued

Chip TAG list

| | | | |
|---|---|---|---|
| 11 | ProbeSet01820 | TCAGCGCGTGTCGTTGCATA [SEQ ID NO: 13] | High |
| 12 | ProbeSet01253 | TTGAATCGTTTGAATCGCGG [SEQ ID NO: 14] | High |
| 13 | ProbeSet01814 | CATGCAGCTCGATCTAGCGA [SEQ ID NO: 15] | High |
| 14 | ProbeSet01790 | CATGCAGCTCGATCTAGCGA [SEQ ID NO: 16] | High |
| 15 | ProbeSet01081 | CTTGATACGACTGTCATGGC [SEQ ID NO: 17] | High |
| HC | ProbeSet00661 | CTTGATACGACTGTCATGGC [SEQ ID NO: 18] | High |

TABLE 2

Chip probe sets 5'→3'

| | |
|---|---|
| 1+ | AGAGCTTAACCACGAGCAGC [SEQ ID NO: 19] |
| 1− | CGTACCAATGGATGCGGTCT [SEQ ID NO: 20] |
| 2+ | AGACCGCATCCATTGGTACG [SEQ ID NO: 21] |
| 2− | CGTACCAATGGATGCGGTCT [SEQ ID NO: 22] |
| 3+ | GAGCTTCGTGAACTGACCTC [SEQ ID NO: 23] |
| 3− | GAGGTCAGTTCACGAAGCTC [SEQ ID NO: 24] |
| 4+ | GATCTAACGCACGGGAACTC [SEQ ID NO: 25] |
| 4− | GAGTTCCCGTGCGTTAGATC [SEQ ID NO: 26] |
| 5+ | GATTAGAGCCACCTAGTCGC [SEQ ID NO: 27] |
| 5− | GCGACTAGGTGGCTCTAATC [SEQ ID NO: 28] |
| 6+ | GATCGGCATCTAGCTTGACT [SEQ ID NO: 29] |
| 6− | AGTCAAGCTAGATGCCGATC [SEQ ID NO: 30] |
| 7+ | ATCCCGTGAGTCGATGGTTT [SEQ ID NO: 31] |
| 7− | AAACCATCGACTCACGGGAT [SEQ ID NO: 32] |
| 8+ | AGTCGATACCTACGCTGCAT [SEQ ID NO: 33] |
| 8− | ATGCAGCGTAGGTATCGACT [SEQ ID NO: 34] |
| 9+ | ACAGGCAGGCAATCGTTGTA [SEQ ID NO: 35] |

TABLE 2-continued

Chip probe sets 5'→3'

| | |
|---|---|
| 9− | TACAACGATTGCCTGCCTGT [SEQ ID NO: 36] |
| 10+ | ATATCCGACTCAGCTCTGTG [SEQ ID NO: 37] |
| 10− | CACAGAGCTGAGTCGGATAT [SEQ ID NO: 38] |
| 11+ | TATGCAACGACACGCGCTGA [SEQ ID NO: 39] |
| 11− | TCAGCGCGTGTCGTTGCATA [SEQ ID NO: 40] |
| 12+ | CCGCGATTCAAACGATTCAA [SEQ ID NO: 41] |
| 12− | TTGAATCGTTTGAATCGCGG [SEQ ID NO: 42] |
| 13+ | TCGCTAGATCGAGCTGCATG [SEQ ID NO: 43] |
| 13− | CATGCAGCTCGATCTAGCGA [SEQ ID NO: 44] |
| 14+ | TGTGCGATCCTACTGACCGT [SEQ ID NO: 45] |
| 14− | ACGGTCAGTAGGATCGCACA [SEQ ID NO: 46] |
| 15+ | GCCATGACAGTCGTATCAAG [SEQ ID NO: 47] |
| 15− | CTTGATACGACTGTCATGGC [SEQ ID NO: 48] |
| HC− | ACGCAGTGAGTAGCATCCTG [SEQ ID NO: 49] |

EXAMPLE 7

Development of Assay Involving Dual Labelled Probes

Figure 4:
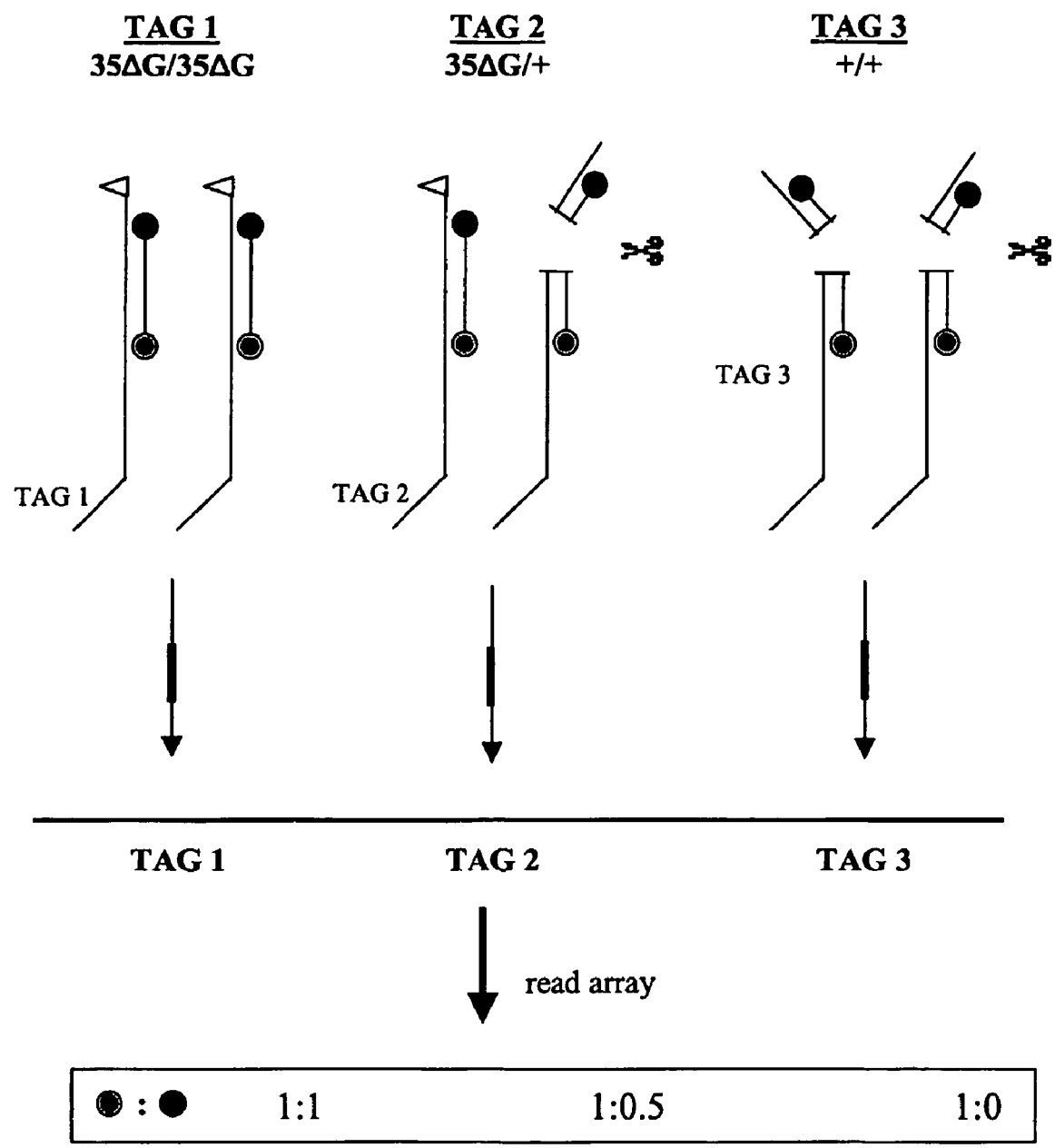
FIG. 4 is a diagram of a genetic assay to determine the homozygous presence or absence or the presence in heterozygous form of the 35ΔG mutation in the connexin 26 gene. This is a modified version of the method described in FIG. 1. The method uses a dually labelled probe which is annealed to single-stranded DNA as they cleaved.

FIG. 4 is a diagrammatic representation of a modified assay involving a dual labelled oligonucleotide primer. The dual lableled primer is connected to single-stranded DNA and then cleaved.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method for determining the presence or absence of a homozygous or heterozygous mutation in a gene, said method comprising:

amplifying a target nucleotide sequence within the gene using a first and a second primer to produce an amplified product, wherein said first primer comprises one or more chemically modified nucleotides, bases or phosphodiester bonds such that a nucleotide strand which extends from said first primer is substantially resistant to exonuclease activity, and wherein said second primer comprises a nucleotide sequence which introduces in the strand extended by said first primer a tag sequence which is complementary to a capture oligonucleotide immobilized to a solid support and wherein one or both of said first or second primers introduces a restriction site in the target sequence when there is no mutation;

digesting the amplified product with an exonuclease to digest the strand not amplified by the primer comprising the exonuclease-resistant nucleotides, bases or phosphodiester linkages to generate a single-stranded nucleic acid molecule;

hybridizing to said single-stranded nucleic acid molecule a probe that contains complementarity to a region encompassing the restriction site that is introduced when no mutation is present to generate a partial double-stranded molecule wherein the probe comprises two reporter molecules capable of facilitating the provision of identifiable signals which can be distinguished from each other;

contacting the partially double-stranded molecules with a restriction endonuclease which will digest the double-stranded molecules which do not contain the mutation and subjecting digested and/or non-digested molecules to conditions to permit annealing of the tag sequence to the capture oligonucleotide immobilized to the solid support;

measuring the relative intensity of the signal by the reporter molecules;

wherein an equal intensity of different signals represents a homozygous presence of the mutation;

wherein one signal represents an absence of the mutation; and wherein a mixture of signals, in which the intensity of one signal is less than the intensity of the other signal thereby represents a heterozygous presence of the mutation.

2. A method for determining the presence or absence of a homozygous or heterozygous mutation in a gene, said method comprising:

amplifying a target nucleotide sequence within the gene using a first and second primer to produce an amplified product, wherein said first primer comprises one or more chemically modified nucleotides, bases or phosphodiester bonds such that a nucleotide strand which extends from said first primer is substantially resistant to exonuclease activity, and wherein said second primer comprises a nucleotide sequence which introduces in the strand extended by said first primer a tag sequence which is complementary to a capture oligonucleotide immobilized to a solid support and wherein one or both of said first or second primers removes a restriction site in the target sequence when there is no mutation;

digesting the amplified product with an exonuclease to digest the strand not amplified by the primer comprising the exonuclease-resistant nucleotides, bases or phosphodiester linkages to generate a single-stranded nucleic acid molecule;

hybridizing to said single-stranded nucleic acid molecule a probe that contains complementarity to a region encompassing the restriction site that is removed when no mutation is present to generate a partial double-stranded molecule wherein the probe comprises two reporter molecules capable of facilitating the provision of identifiable signals which can be distinguished from each other;

contacting the partially double-stranded molecules with a restriction endonuclease which will digest the double-stranded molecules which contain the mutation and subjecting digested and/or non-digested molecules to conditions to permit annealing of the tag sequence to the capture oligonucleotide immobilized to the solid support;

measuring the relative intensity of the signal by the reporter molecules wherein an equal intensity of different signals represents a homozygous absence of the mutation;

wherein one signal represents a homozygous mutation; and wherein a mixture of signals, in which the intensity of one signal is less than the intensity of the other signal thereby represents a heterozygous presence of the mutation.

3. A method of claim 1 or 2 wherein the solid support is selected from the list comprising glass and a polymer such as cellulose, nitrocellulose, ceramic material, polyacrylamide, nylon, polystyrene and its derivatives, polyvinylidene difluoride, methacrylate and its derivatives, polyvinyl chloride and polypropylene.

4. A method of claim 3 wherein the solid support is glass.

5. A method of any one of claims 1 to 2 wherein two or more oligonucleotide sequences are anchored to the solid support in the form of an array.

6. A method any one of claims 1 to 2 wherein the restriction endonuclease site is recognized by a restriction enzyme selected from the list comprising AatI, AatII, AauI, Acc113I, Acc16I, Acc65I, AccB1I, AccB7I, AccBSI, AccI, AccII, AccIII, AceIII, AciI, AclI, AclNI, AclWI, AcsI, AcyI, AdeI, AfaI, AfeI, AflII, AflIII, AgeI, AhaIII, AhdI, AluI, Alw21I, Alw26I, Alw44I, AlwI, AlwNI, Ama87I, AocI, Aor51HI, ApaBI, ApaI, ApaLI, ApoI, AscI, AseI, AsiAI, AsnI, Asp700I, Asp718I, AspEI, AspHI, AspI, AspLEI, AspS9I, AsuC2I, AsuHPI, AsuI, AsuII, AsuNHI, AvaI, AvaII, AvaIII, AviII, AvrII, AxyI, BaeI, BalI, BamHI, BanI, BanII, BanIII, BbeI, BbiII, BbrPI, BbsI, BbuI, Bbv12I, BbvCI, BbvI, BbvII, BccI, Bce83I, BcefI, BcgI, BciVI, BclI, BcnI, BcoI, BcuI, BetI, BfaI, BfiI, BfmI, BfrI, BglI, BglII, BinI, BlnI, BlpI, Bme18I, BmgI, BmrI, BmyI, BpiI, BplI, BpmI, Bpu10I, Bpu1102I, Bpu14I, BpuAI, Bsa29I, BsaAI, BsaBI, BsaHI, BsaI, BsaJI, BsaMI, BsaOI, BsaWI, BsaXI, BsbI, Bsc4I, BscBI, BscCI, BscFI, BscGI, BscI, Bse118I, Bse1I, Bse21I, Bse3DI, Bse8I, BseAI, BseCI, BseDI, BseGI, BseLI, BseMII, BseNI, BsePI, BseRI, BseX3I, BsgI, Bsh1236I, Bsh1285I, Bsh1365I, BshI, BshNI, BsiBI, BsiCI, BsiEI, BsiHKAI, BsiI, BsiLI, BsiMI, BsiQI, BsiSI, BsiWI, BsiXI, BsiYI, BsiZI, BsII, BsmAI, BsmBI, BsmFI, BsmI, BsoBI, Bsp106I, Bsp119I, Bsp120I, Bsp1286I, Bsp13I, Bsp1407I, Bsp143I, Bsp143II, Bsp1720I, Bsp19I, Bsp24I, Bsp68I, BspA2I, BspCI, BspDI, BspEI, BspGI, BspHI, BspLI, BspLU11I, BspMI, BspMII, BspTI, BspXI, BsrBI, BsrBRI, BsrDI, BsrFI, BsrGI, BsrI, BsrSI, BssAI, BssHII, BssKI, BssNAI, BssSI, BssT1I, Bst1107I, Bst2BI, Bst2UI, Bst4CI, Bst71I, Bst98I, BstACI, BstAPI, BstBAI, BstBI, BstDEI, BstDSI, BstEII, BstF5I, BstH2I, BstHPI, BstMCI, BstNI, BstNSI, BstOI, BstPI, BstSFI, BstSNI, BstUI, BstX2I, BstXI, BstYI, BstZ17I, BstZI, Bsu15I, Bsu36I, Bsu6I, BsuRI, BtgI, BtsI, Cac8I, CauII, CbiI, CciNI, CelII, CfoI, Cfr10I, Cfr13I, Cfr42I, Cfr9I, CfrI, CjeI, CjePI, ClaI, CpoI, Csp45I, Csp6I, CspI, CviJI, CviRI, CvnI, DdeI, DpnI, DpnII, DraI, DraII, DraIII, DrdI, DrdII, DsaI, DseDI, EaeI, EagI, Eam1104I, Eam1105I, EarI, EciI, Ec136II, EclHKI, EclXI, Eco105I, Eco130I, Eco147I, Eco24I, Eco255I, Eco31I, Eco32I, Eco47I, Eco47III, Eco52I, Eco57I, Eco64I, Eco72I, Eco81I, Eco88I, Eco91I, EcoICRI, EcoNI, EcoO109I, EcoO65I, EcoRI, EcoRII, EcoRV, EcoT14I, EcoT22I, EcoT38I, EgeI, EheI, ErhI, Esp1396I, Esp3I, EspI, FauI, FauNDI, FbaI, FinI, Fnu4HI, FnuDUII, FokI, FriOI, FseI, Fsp4HI, FspI, GdiII, GsuI, HaeI, HaeII, HaeIII, HaeIV, HapII, HgaI, HgiAI, HgiCI, HgiEI, HgiEII, HgiJII, HhaI, Hin1I, Hin2I, Hin4I, Hin6I, HincII, HindII, HindIII, HinfI, HinP1I, HpaI, HpaII, HphI, Hsp92I, Hsp92II, HspAI, ItaI, KasI, Kpn2I, KpnI, Ksp22I, Ksp632I, KspAI, KspI, Kzo9I, LspI, MaeI, MaeII, MaeIII, MamI, MbiI, MboI, MboII, McrI, MfeI, MflI, MlsI, MluI, MluNI, Mly113I, MmeI, MnlI, Mph1103I, MroI, MroNI, MroXI, MscI, MseI, MslI, Msp17I, MspA1I, MspCI, MspI, MspR9I, MstI, MunI, Mva1269I, MvaI, MvnI, MwoI, NaeI, NarI, NciI, NcoI, NdeI, NdeII, NgoAIV, NgoMIV (previously known as NgoMI), NheI, NlaIII, NlaIV, NotI, NruGI, NruI, NsbI, NsiI, NspBII, NspI, NspV, PacI, PaeI, PaeR7I, PagI, PalI, PauI, Pfl1108I, Pfl23II, PflFI, PflMI, PinAI, Ple19I, PleI, PmaCI, Pme55I, PmeI, PmlI, Ppu10I, PpuMI, PshAI, PshBI, Psp124BI, Psp1406I, Psp5II, PspAI, PspEI, PspLI, PspN4I, PspOMI, PspPPI, PstI, PvuI, PvuII, RcaI, RleAI, RsaI, RsrII, SacI, SacII, SalI, SanDI, SapI, Sau3AI, Sau96I, SauI, SbfI, ScaI, SchI, ScrFI, SdaI, SduI, SecI, SexAI, SfaNI, SfcI, SfeI, SfiI, SfoI, Sfr274I, Sfr303I, SfuI, SgfI, SgrAI, SimI, SinI, SmaI, SmiI, SmlI, SnaBI, SnaI, SpeI, SphI, SplI, SrfI, Sse8387I, Sse8647I, Sse9I, SseBI, SspBI, SspI, SstI, SstII, StuI, StyI, SunI, SwaI, TaiI, TaqI, TaqII, TatI, TauI, TfiI, ThaI, TruII, Tru9I, TscI, TseI, Tsp45I, Tsp4CI, Tsp509I, TspEI, TspRI, Tth111I, Tth111II, TthHB8I, UbaDI, UbaEI, UbaLI, UbaOI, Van91I, Vha4641, VneI, VspI; XagI, XbaI, XcmI, XhoI, XhoII, XmaCI, XmaI, XmaIII and XmnI, Zsp2I.

7. A method of any one of claims 1 to 2 wherein the reporter molecule is selected form the list comprising chloramphenicol, a colourless galactosidase, a colourless glucuronide, luciferin and green fluorescent protein.

8. A method of any one of claims 1 to 2 wherein the target nucleotide sequence is in a eukaryotic cell.

9. A method of claim 8 wherein the cell is a mammalian cell.

10. A method of claim 9 wherein the mammalian cell comprises a target sequence, wherein a mutation is associated with a disease condition.

* * * * *